United States Patent [19]
Abe et al.

[11] Patent Number: 5,684,249
[45] Date of Patent: Nov. 4, 1997

[54] GROUND VIBRATION PROPERTIES DETECTION METHOD AND EQUIPMENT THEREOF

[75] Inventors: Yorimasa Abe, Suginamiku; Kiyotaka Hisano, Fukuokaken; Kazuhiro Yamamoto, Fukuokaken; Minoru Honda, Fukuokaken, all of Japan

[73] Assignees: Fe Lime Industry Corporation; Western Japan Geography Survey Co., Ltd., both of Fukuokaken, Japan

[21] Appl. No.: 579,826

[22] Filed: Dec. 28, 1995

[30] Foreign Application Priority Data

Nov. 15, 1995 [JP] Japan .................................. 7-296824

[51] Int. Cl.[6] .............................. G01M 7/00; G01N 3/42
[52] U.S. Cl. .................... 73/146; 73/12.13; 73/82; 73/579
[58] Field of Search ........................... 73/146, 12.06, 73/12.13, 79, 82, 84, 579

[56] References Cited

U.S. PATENT DOCUMENTS

| | | | |
|---|---|---|---|
| 3,888,108 | 6/1975 | Brands | 73/146 X |
| 4,020,672 | 5/1977 | Safford | 73/12.06 X |
| 4,163,393 | 8/1979 | Gutierrez et al. | 73/12.01 X |
| 4,405,020 | 9/1983 | Rassieur | 73/84 X |
| 4,881,405 | 11/1989 | Paquet | 73/146 |

*Primary Examiner*—George M. Dombroske
*Assistant Examiner*—Joseph L. Felber
*Attorney, Agent, or Firm*—Longacre & White

[57] ABSTRACT

The present disclosure concerns a ground vibration properties detection method by generating a specified vibration load equal to the actual load generated by traffic vehicles on a paved road or by generating a specified vibration load corresponding to a seismic intensity of earthquake on a ground and measuring the vibration load as a vibration level induced by the vibration load and equipment thereof.

4 Claims, 9 Drawing Sheets

GROUND VIBRATION PROPERTIES DETECTION METHOD AND EQUIPMENT THEREOF

BACKGROUND OF THE INVENTION

1. Field of the invention

This invention relates to a detection method of vibration properties of a ground, for instance, a road pavement construction or a cushion course of an architecture construction foundation and equipment thereof.

2. Description of the Prior Art

Design of a road pavement or an evaluation method after the road pavement constructed has been based on the number of vehicles passed on the road or an impact load which is not the real vibration load but an assumption.

The design of a pavement is being made as per the methods shown in "Asphalt Pavement Guideline" and "Cement Concrete Pavement Guideline" published by The Japan Highway Association.

Basically, a destructive load to a road is given in terms of the member of passed heavy vehicles each giving 10,000 times the action by an ordinary car and the road load classes (Designed Traffic Classification) are classified as shown in Table 1 (L to D Traffics).

Generally, the pavement thickness is determined by a graph (allegedly based on the result of AASHO Road Test conducted in California approximately 50 years ago) experimentally prepared from the relationship between the classification and the supporting force ($K_{30}$ value of CBR and Flat Plate Loading Test) of the road bed (base ground supporting the pavement).

TABLE 1

Designed Traffic Classification and the Corresponding Designed Wheel Loads

| Designed Traffic Class | Heavy Vehicles Traffic (No./Day) | Designed Wheel Load |
|---|---|---|
| L Traffic | Below 100 | 2 tons |
| A Traffic | Above 100 Below 250 | 3 tons |
| B Traffic | Above 250 Below 1,000 | 5 tons |
| C Traffic | Above 1,000 Below 3,000 | 8 tons |
| D Traffic | Above 3,000 | 12 tons |

The designed wheel loads in Table 1 were obtained by conversions calculated from the total traffic loads into a wheel load based on which it is theoretically possible to design an economical pavement structure suitable for a road bed supporting force by calculating physically the deflection of or strain generated by asphalt or concrete plate. However, the supporting force is not always uniform over the traffic road and the properties assumed for the calculation of the pavement construction materials do not conform to the actual values.

The wheel loads are supported 3-dimensionally and the deflection is variable depending on the part or the distance from the loading point. Further the calculation must be made under such a difficult condition as continuous vibration load. Therefore, if no confirmation is made by experiment, any values obtained even from such a complex calculation should be adapted only for reference.

The vibration damping function of pavement is variable depending on the materals of the ground including improved road bed and the construction technology and is an important factor for the counter-measures to traffic road vibration.

The vibration damping function can be evaluated by giving a specified dynamic load to a road surface and by measuring each vibration level at each specified point spaced from the vibration origin. Conventional methods for measuring vibration by giving an impact to road surface are as follows:

The Japan Highway Public Corporation uses a method having a large dump truck loaded full of mud run onto a pile of square lumbers and stoping the truck to drop the tires from the lumbers to give an impact to the road surface and measuring the vibration thereof.

FWD pavement checking system (Falling Weight Deflectometer (FWD) Deflection Measuring Unit) is to give an impact to the surface of the pavement by dropping a heavy weight by means of a load plate of 30 cm diameter and measure the deflection generated on the road surface by a sensor located on a half diameter from the load center to learn the properties of the pavement construction. The method of giving an impact by dropping the tires from the square lumbers on the road surface is only a single impact load and is not the number of vehicles passed (not a load) or the actual vibration load for designing the road pavement or for assumption of the evaluation after the pavement. Therefore, there is a problem that the loading load is rather less than the designed wheel load and is not the actual traffic load given by continuous vibration load. The single load is unable to give a load corresponding to the designed wheel load shown in Table 1 and is also unable to generate a vibration load identical to the actual load generated by the traffic vehicles. In addition, the traffic vehicles are given with a forced vibration resulted from uneven road surface and as the reaction the vibration and the impact load are transferred to the road surface through the tires and a large dynamically added load is generated. This is the origin of the traffic vibration on the roads.

The FWD impact load of FWD Deflection Measuring Unit described above is against a static load (ground contact pressure) and not for a dynamically added load.

In the case that the ground is a cushion course of architecture construction foundation, there was no way to generate a vibration level corresponding to an earthquake amplitude and therefore it was impossible to detect the actual vibration properties.

SUMMARY OF THE INVENTION

An objective of this invention is to provide a method of detecting a vibration properties of ground by generating a specified vibration load equal to the actual load generated by traffic vehicles on the ground of a road pavement construction and by generating a vibration load corresponding to the seismic intensity of earthquake and detect the vibration level induced by the vibration load on the ground of a cushion course of architecture construction foundation and equipment thereof.

In order to meet the above objective, the present invention is, in the case that the ground is a road pavement construction, to drop vertically a heavy weight having a specified head on a road pavement once or continuously every unit time to give a dynamically added load corresponding to the designed wheel load generated by the traffic vehicles on a standard flat road surface and to measure the vibration generated therefrom as a vibration level at each distance from the vibration origin.

In the case that the ground is a cushion course of architecture construction foundation, the heavy weight having a specified height is dropped vertically on the ground once or continuously every unit time to give to the ground a load corresponding to a seismic intensity of earthquake and to measure the vibration generated therefrom as a vibration level at each distance from the vibration origin. The equipment of performing the above method comprises a vibrator and a measuring unit of vibration level, the vibrator comprising a driving motor, a driving sprocket wheel mounted on output shaft of the driving motor, a driven sprocket provided in spaced relationship with the driving sprocket, a first roller chain provided between the driving sprocket and the driven sprocket, a driving sprocket wheel lifting a heavy weight transmitting a rotating force of the driven sprocket, a driven sprocket wheel mounted on the upper portion of the sprocket wheel lifting the heavy weight lifting the heavy weight, a second roller chain provided between the driving sprocket wheel lifting the heavy weight and the driven sprocket wheel lifting the heavy weight, an electro-magnetic clutch provided between the driven sprocket wheel and the driving sprocket wheel lifting the heavy weight to put off or put on the rotating force by a signal from each limit switch at a predetermined upper position and lower position, a wire rope fastening fitting mounted on the second roller chain and traveling vertically between the lower area of the driving sprocket wheel lifting the heavy weight and the upper area of the driven sprocket wheel lifting the heavy weight, a lifting rope an end of which is connected with the wire rope fastening fitting and hanging via a wire rope guide roller and a heavy weight hung on the other end of the lifting wire rope. Said vibration level measuring unit is comprised of a sensor to detect the vibration level at each distance from a place where the heavy weight of the vibration generating unit is dropped, a vibration level meter connected with the sensor to measure the vibration level and a vibration level recorder connected with the vibration level meter to record the vibration level measured.

DESCRIPTION OF THE PREFERRED EMBODIMENTS

The preferred embodiments of this invention are described hereunder with reference to the accompanying drawings:

Skeltons of a vibration generating unit 100 and a vibration level measuring unit 200 according to the present invention are shown in FIG. 1(a) and FIG. 1(b) to describe an evaluation method of vibration damping function of pavement.

Figure 1:
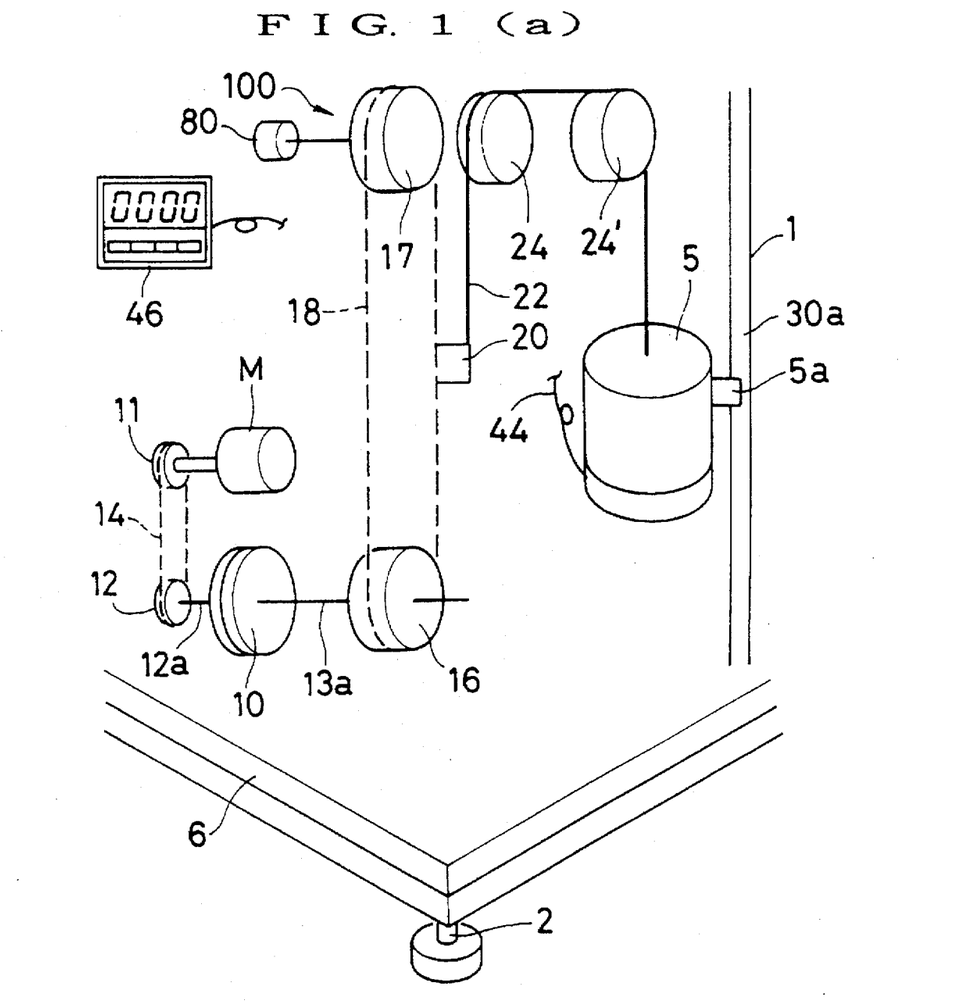
FIG. 1(a) is a perspective drawing showing a skelton of the vibration generating unit 100 according to the present invention to describe the evaluation method of vibration damping function of pavement.
FIG. 1(b) is a perspective drawing showing a skelton of the vibration level measuring unit 200 accordng to the present invention to describe the evaluation method of vibration damping function of pavement.
Figure 2:
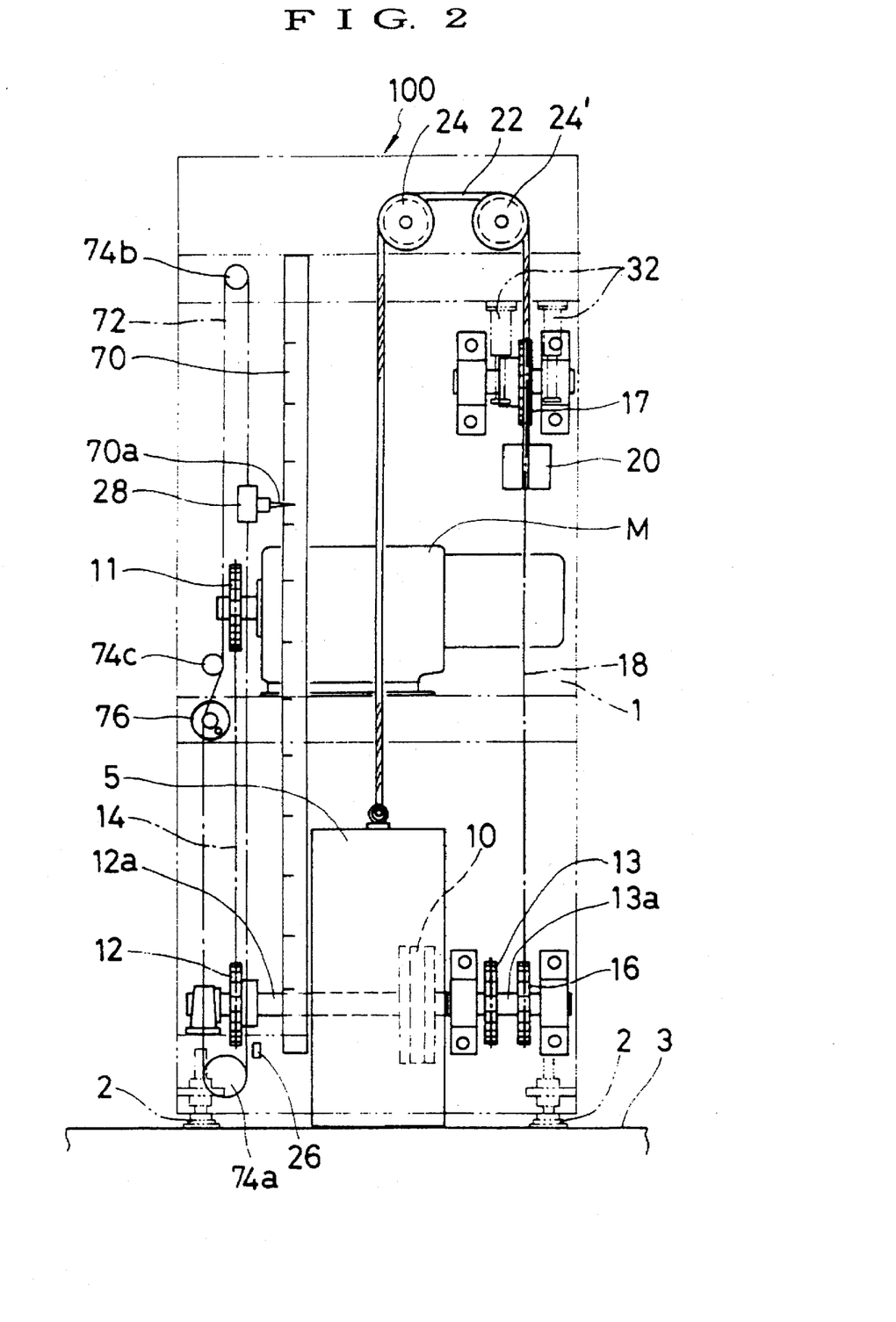
FIG. 2 is a front elevation of the vibration generating unit.
Figure 3:
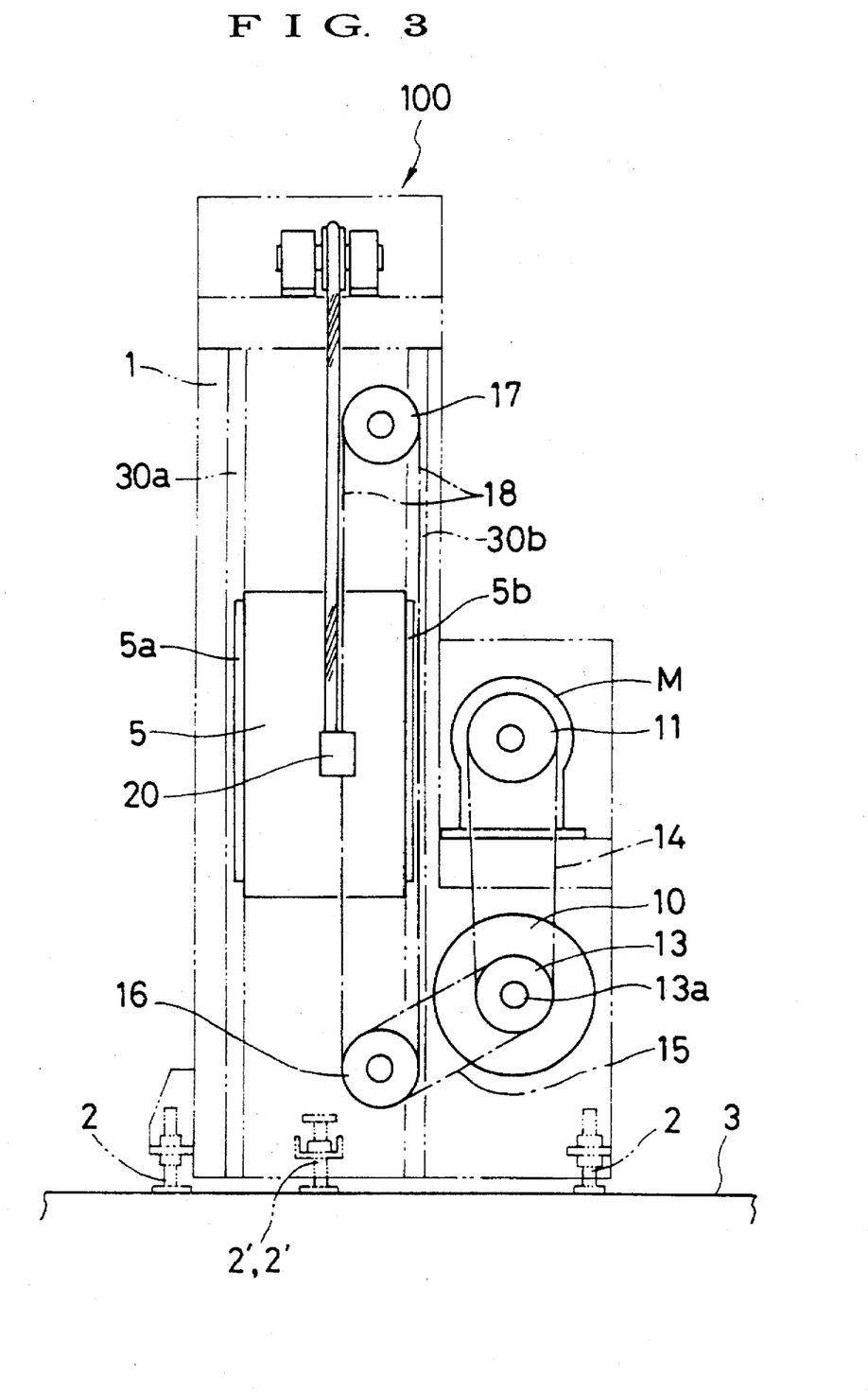
FIG. 3 is a side elevation of the vibration generating unit.

The construction of the vibration generating unit 100 is shown in FIG. 1(a), FIG. 2 and FIG. 3. A supporting stand 1 is positioned on a paved road surface 3 by means of at least three supporting legs 2, 2 and 2 having an installation level adjustable cushion each provided on bottom thereof. A driving motor M is mounted on the middle of the supporting stand 1 and a driving sprocket wheel 11 is installed on output shaft thereof. A driven sprocket wheel 12 is provided underneath the driving sprocket wheel 11 and a first roller chain 14 is provided between both sprocket wheels 11 and 12. The output of the driving motor M is transferred to the driven sprocket wheel 12, then to the driving sprocket wheel 16 lifting the heavy weight via a power transfer sprocket wheel 13 and an auxiliary roller chain 15. An electromagnetic clutch 10 is provided between a shaft 12a of the driven sprocket wheel 12 and a shaft 13 of a shaft 13a of the power transfer sprocket wheel 13 to turn off or turn on the coupling between both shafts 12a and 13a.

A driven sprocket wheel 17 for lifting the heavy weight is provided above the driving sprocket wheel for lifting the heavy weight and a second roller chain 18 is provided between both sprocket wheels 16 and 17.

A wire rope fastening fitting 20 is mounted on the second roller chian 18 at a specified position and one end of the lifting wire 22 is tied with the wire rope fastening fitting 20. The lifting wire rope 22 is hung by means of wire rope guide rollers 24 and 24' with a heavy weight 5 hung from the other end of the rope. The wire rope fastening fitting 20, which is mounted on the second roller chain 18, moves vertically between the lower area close to the driving sprocket wheel 16 for lifting the heavy weight and the upper area close to the driven sprocket wheel 17 for lifting the heavy weight by the action of the electromagnetic clutch 10 which transfers the driving force of the driving motor M in response to a signal from limit-switches 26 and 28 defining the lower limit and the upper limit as described hereunder.

The electromagnetic clutch 10 is turned on when the heavy weight is to be lifted and is turned off from nearly starting of the heavy weight dropping until the next lifting thereof to generate a vibration force when dropped from a specified lifting height with a specified interval by regulating the times of the turning-on or turning-off.

Figure 4:
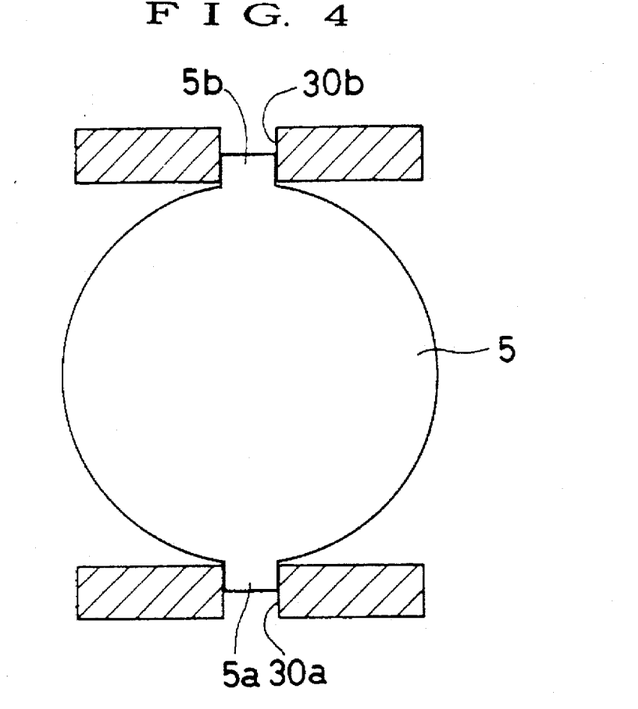
FIG. 4 is a cross sectional view indicating the heavy weight guide mechanism of the vibration generating unit.

As shown in the enlarged view in FIG. 4 both sides of the heavy weight 5 are provided with projected splines 5a and 5b.

A heavy weight guide mechanism 30 having receiving slots 30a and 30b formed along the direction of heavy weight dropping is provided on the supporting stand 1 to secure a stable dropping of the heavy weight 5 with the projected splines 5a and 5b engaged in the receiving slots 30a and 30b respectively. A shock absorber 32 is provided on both sides around the lifting wire rope 22 above the wire rope fastening fitting 20 so that the lifting rope 22 may not be slackened by a shock of inertia expected to be caused when the heavy weight 5 is dropped on the ground.

Figure 5:
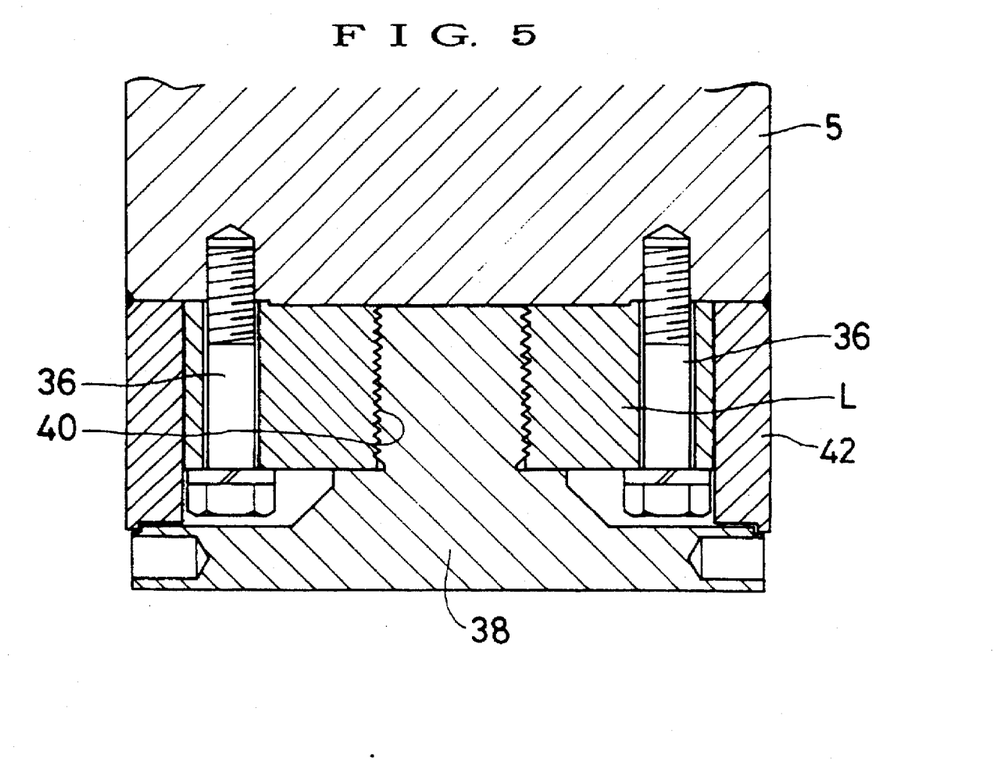
FIG. 5 is a vertically sectional view indicating the heavy weight structure.

FIG. 5 shows the heavy weight 5 which is mounted with a load cell L by means of a plurality of fastening bolts 36 on the lower end thereof and a cylindrical inclusion part 42 is engaged thereon externally and a shock plate 38 is fastened underneath thereof by screwing into a screw-in portion 40 formed in the center of the load cell L. The output from the load cell L is taken as an electric signal and modulated to show on a digital display of the impact load of the heavy weight 5 on a strain type indicater 46 (refer to FIG. 1) for a sensor.

Figure 6:
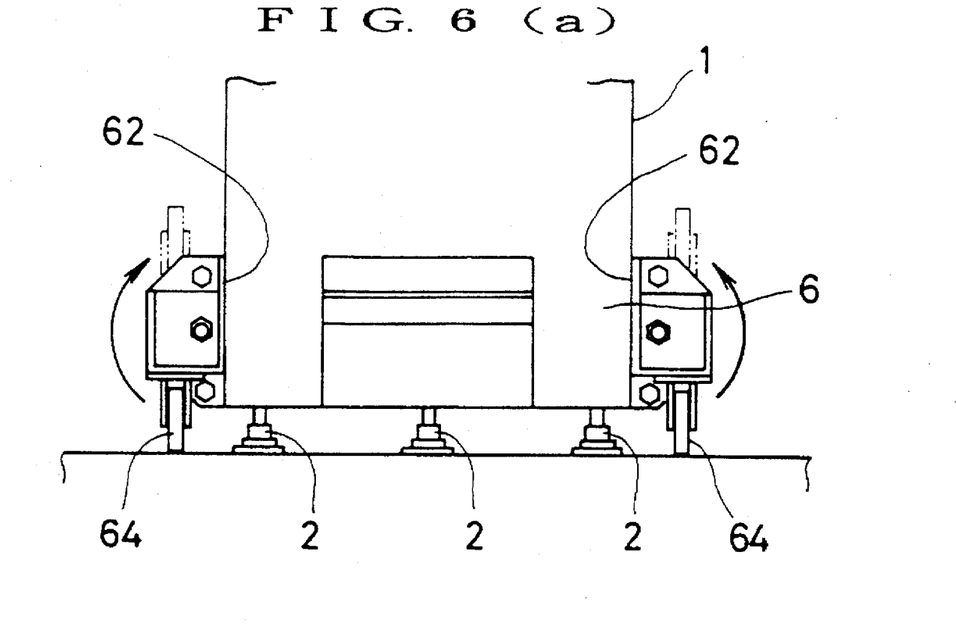
FIG. 6(a) is a front elevation indicating the lower structure of the vibration generating unit.
FIG. 6(b) is a side elevation indicating the lower structure of the vibration generating unit.

FIG. 6(a) and FIG. 6(b) are the front elevation and the side elevation showing the structure of a base board 6 of the supporting stand 1 respectively. The supporting stand is positioned on the paved road surface by means of at least 3 supporting legs 2, 2 and 2 having an installation level adjustable cushion, each provided on the bottom thereof.

Figure 7:
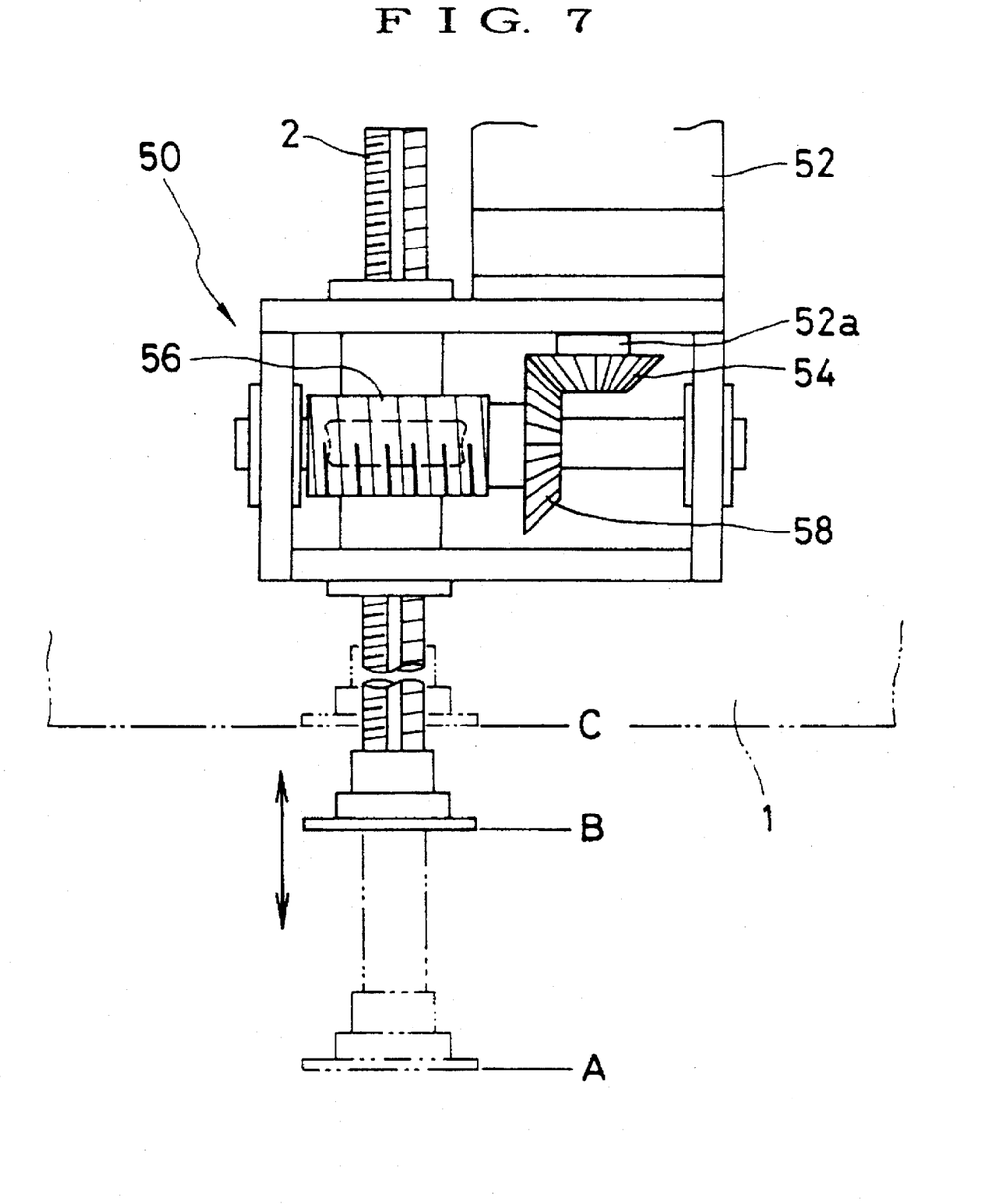
FIG. 7 is a sectional view showing the supporting legs of the vibration generating unit.
Figure 8:
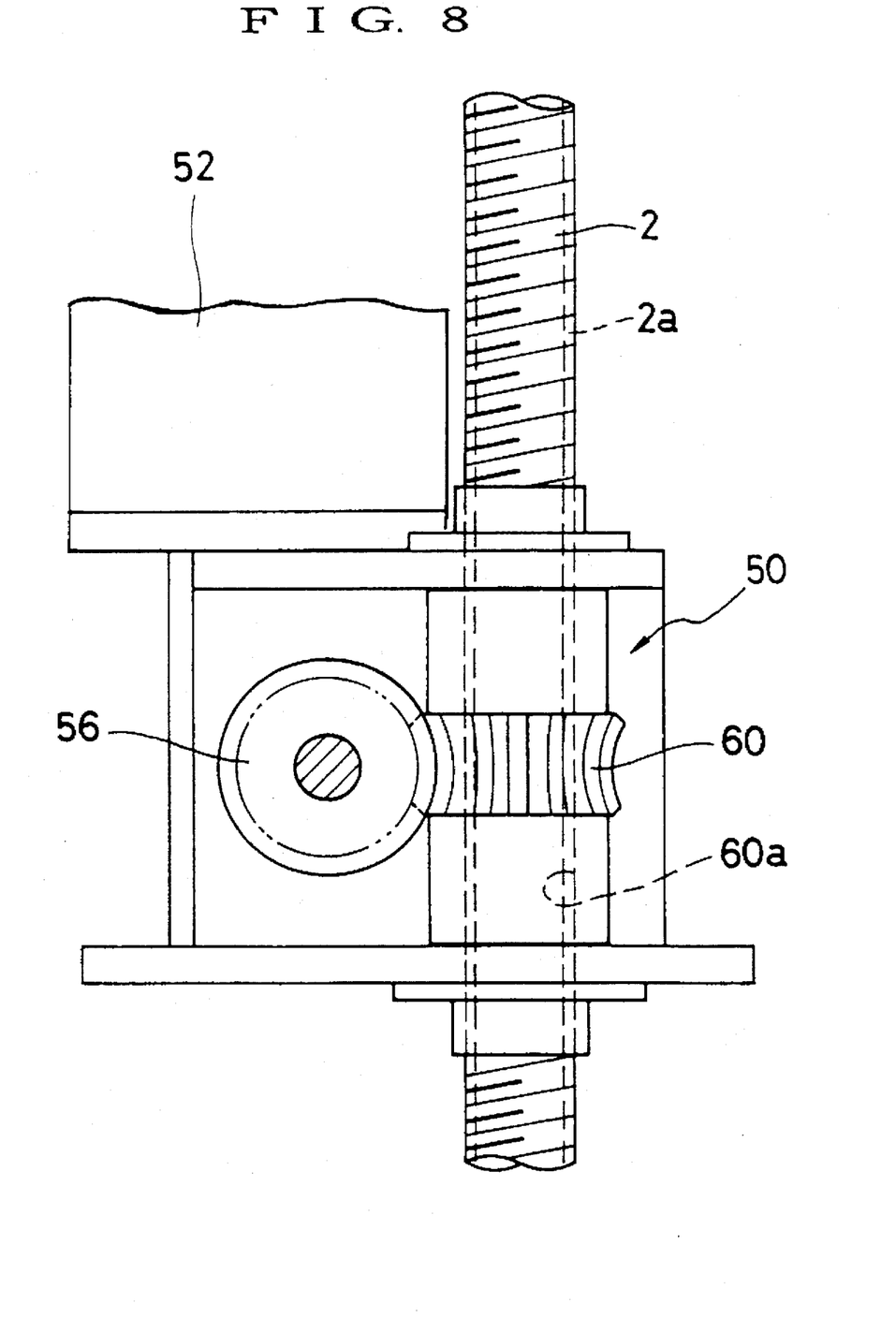
FIG. 8 is a side elevation showing the supporting legs of the vibration generating unit.

The supporting leg 2 is of an electric worm adjusting jack construction and a jack 50 shown in FIG. 7 and FIG. 8 is mounted on a frame (not shown) provided on the lower portion (3 points) of the supporting stand 1. The jack 50 is comprised of a 3-phase AC induction motor 52 the output shaft 52a of which is mounted with a bevel gear 54 with which a level gear 58 fastened on a shaft end of a worm gear 56 is engaged. The worm gear 56 is engaged with a worm wheel gear 60 as shown in FIG. 8 through which the supporting leg 2 is axially inserted. The worm wheel gear 60 is provided with an internal teeth 60a which is engaged with an elevating screwed shaft 2a of the supporting leg 2. Hence, revolution of the output shaft of the 3-phase AC induction motor transfers the output to the worm wheel gear 60 via the worm gear 56 to move the supporting leg 2 vertically.

As shown in FIG. 6(a) and FIG. 6(b) the supporting table is provided on the 4 corners with a wheel mounting fitting 62 each on which a wheel is rotatably mounted. Each wheel mounting fitting 62 is connected with each other by means of a shaft 66 passing through therein and is axially rotatable with regard to the shaft 66 and a wheel 64 can be fastened either at the position indicated by a solid line or at the position indicated by a dotted line as shown in FIG. 6(a).

This unit is operated by extending the supporting legs 2, 2, and 2 from the present position to position A as shown in FIG. 7 by means of the jack 50 to float up the wheel 64 and the wheel mounting fitting 62 is swung up as indicated by arrow to inverse the wheel 64. Under this condition, the supporting legs 2, 2 and 2 are moved backward to the position B as shown in FIG. 7 to act the vibration. In additon to the supporting legs 2, 2 and 2, manual auxiliary jacks 2' and 2' are installed on both sides symmetrically to make a 5-point supporting as indicated in FIG. 3 in order to secure the stability when the impact is given.

After the evaluation test is completed with this equipment, the supporting legs 2, 2 and 2 are again extended to the position A by the jack 50 as shown in FIG. 7 to return the wheel 64 to the position shown by the solid line from the position on the dotted line. Then, the supporting legs 2, 2 and 3 are moved backward by the jack 50 to the position C in FIG. 7 to land the wheel 64 and now this equipment can be moved freely on the paved road.

As shown in FIG. 2, a longitudinal scale plate 70 is mounted on the front side of supporting stand 1 and a lower limit switch 26 is installed underneath thereof. A height adjusting chain 72 is provided in parallel to the scale plate 70 on which an upper limit switch 28 is installed for reading the position indicated by a pointer 70a on the scale plate 70.

The height adjusting chain 72 is provided endlessly by means of guide rolls 74a, 74b and 74c. The height of the upper limit switch 28 can be adjusted by turning a handle 76 rightward or leftward. The electromagnetic clutch 10 transfers or shuts the driving force of the driving motor M by means of a signal from the lower or the upper limit switches 26 and 28.

When a signal from the lower limit switch 25 is detected, the electromagnetic clutch 10 is turned on to connect a shaft 12a of the driven sprocket wheel 12 with a shaft 13a of the power driving sprocket wheel 13 to have the second roller chain 18 move the wire rope fastening fitting 20 downward from the upper area close to the sprocket wheel 16 for lifting the heavy weight and lift the heavy weight 5 by means of the lifting wire rope 22. When the heavy weight 5 is lifted to a specified height and the upper limit switch 28 works, the electromagnetic clutch 10 is turned off and the driving force of the driving motor M is shut off to drop the heavy weight 5 freely. The lower limit switch 26 works just before the heavy weight 5 reaches the road surface and the above operation is repeated to put approximately one load per second on the road surface.

A tachometer 80 is connected with a shaft end of the driven sprocket wheel 17 for lifting the heavy weight 5 to measure the dropping height of the heavy weight 5 by converting the rotation angle of the driven sprocket wheel 17 to the lifting distance by means of an additional unit which is not shown.

Figure 9:
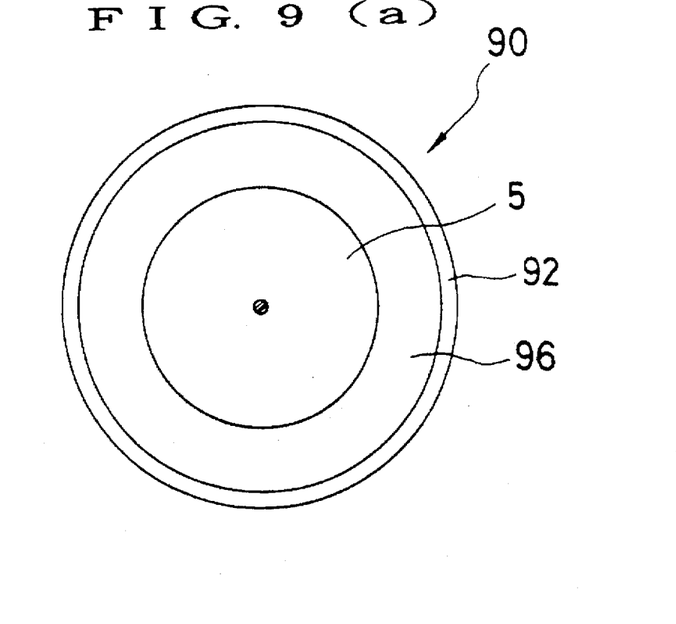
FIG. 9(a) is a top view showing uneven correction mechanism provided on the ground where the heavy weight drops.
FIG. 9(b) is a sectional side elevation showing uneven correction mechanism provided on the ground where the heavy weight drops.

FIG. 9(a) and FIG. 9(b) are the top view and the sectional side elevation of the uneven road surface correction mechanism 90 respectively. The uneven road surface correction mechanism 90 has a larger diameter than that of the heavy weight 5 and comprises a cylindrical frame 92 the upper and lower ends of which are open and filled with a plasticized material 94 and a sound absorbent 96 (synthetic fiber, etc.) is placed thereon. The frame 92 is placed so as to coincide its center with the center of the heavy weight 5.

The plasticized material 94 is to absorb the undulation of the ground surface and flattens the working surface of the ground to which the vibrating force is acted.

The frame 92 prevents the plasticized material 94 from deforming and stabilizes the vibrating force acted. The sound absobent 96 reduces the impact sound generated when the vibrating force is acted.

FIG. 1(b) is a perspective drawing of a vibration level measuring unit 200 to measure each vibration level at each distance from the position where the heavy weight of the vibration generating unit drops.

The vibration level measuring unit 200 comprises a vibration sensor 110 placed at a separate distance from the position where the heavy weight drops, a vibration level meter 120 connected with the vibration sensor 110 and to measure a low frequency vibration level and a vibration level recorder 130 to record the vibration level measured.

The vibration level meter is to have the performance equal to or more than that specified in Japanese Industrial Standard C 1510 and the (JIS) vibration level recorder is also equal to or more than that specified in JIS C 1512.

The measuring method is in accordance with "PAVEMENT TEST HANDBOOK 7–6".

EXAMPLE

The examples of a vibration generating unit and a vibration level measuring unit are described hereunder.

In the case that the ground is of a paved road construction, a load given to the ground can be shown in terms of a wheel load. While vehicles are traveling on a road, a dynamic total load, which is the wheel load plus a dynamic added load generated depending on both of the flatness of the road surface and the travelling velocity of the vehicles corresponding to the wheel load, is actually given to the road surface. Table 2 shows a dynamic added load and a dynamic total load corresponding to a designed wheel load where vehicles are traveling on a road having a standard flatness at a standard velocity (40 km/H).

TABLE 2

DYNAMIC TOTAL LOAD CORRESPONDING TO DESIGNED WHEEL LOAD
(Standard Flatness: 3.5 mm, Standard Velocity: 40 km/H)

| Designed Traffic Class | Designed Wheel Load | Dynamic Coefficient | Dynamic Added Load | Dynamic Total Load |
|---|---|---|---|---|
| L Traffic | 2 ton | 0.42 | 0.84 ton | 2.84 ton |
| A Traffic | 3 ton | 0.42 | 1.26 ton | 4.26 ton |
| B Traffic | 5 ton | 0.42 | 2.10 ton | 7.10 ton |
| C Traffic | 8 ton | 0.42 | 3.36 ton | 11.36 ton |
| D Traffic | 12 ton | 0.42 | 5.04 ton | 17.04 ton |

The dynamic coefficient(iFm) = Dynamic Added Load(Fm)/Designed Wheel Load(Fs) is variable depending on the road surface flatness and the traveling velocity.

Figure 10:
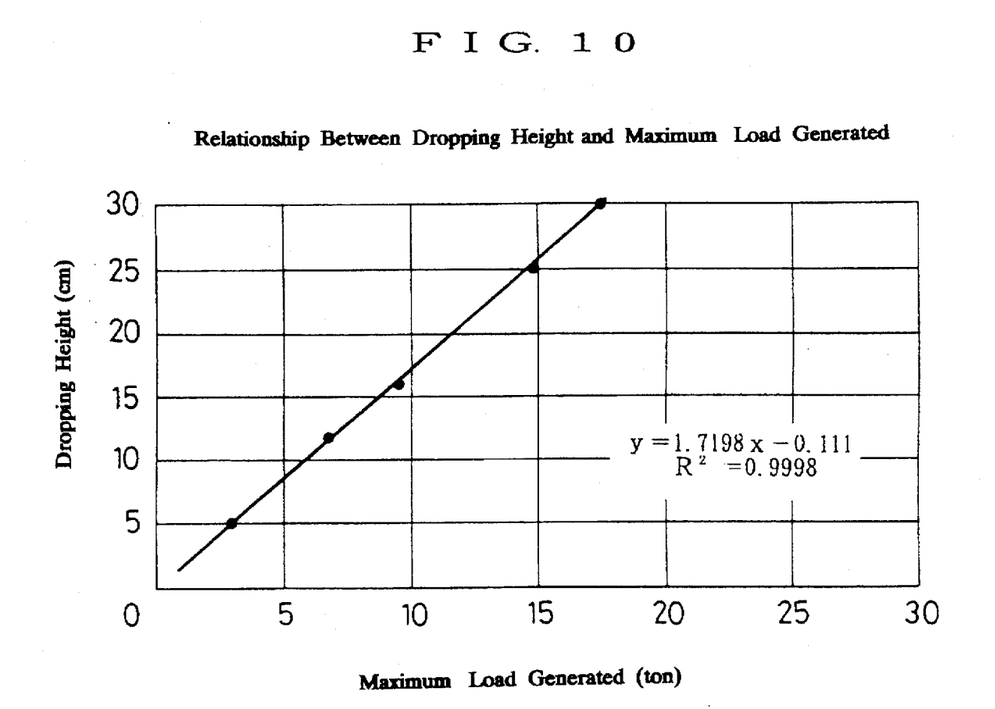
FIG. 10 is a graph showing the relationship between the dropping height of the heavy weight and the maximum load generated.

FIG. 10 shows dropping heights of a heavy weight (a column of 30 cm dia. and 63 cm high) made of iron (density:7.86 kg/cm$^3$) weighing 350 kg dropped freely and measured the maximum loads generated. A asphalt mixture having an average 1.5 cm thickness was laid on an asphalt paved road surface to correct the slope and the uneven road surface and a rubber mat having a 1.5 cm thickness was further laid thereon as a cushion. Then, the load generated was measured by means of a load cell provided on the bottom of the heavy weight.

Therefore, the dropping height of the heavy weight can be obtained from formula (1) to generate each dynamic added load corresponding to each wheel load in the case that the traveling is made on a road surface having a standard flatness (3.5 mm) as shown in Table 2 at a standard velocity on a general road as follows:

$$y = 1.7198x - 0.111 \quad (1)$$

herein, y: dropping height (cm)
x: maximum generated load (ton)

According to the formula (1), the dropping height of the heavy weight necessary to generate each dynamic added load corresponding to each wheel load listed in Table 2 can be obtained as shown in Table 3.

TABLE 3

Dropping Height of Heavy Weight to Generate Dynamic Added Load Corresponding th Designed Wheel Load
(Asphalt Covering: 1.5 cm, Rubber Mat Thickness: 1.5 cm)

| Designed Traffic Class | Designed Wheel Load | Dynamic Added Load | Dynamic Total Load | Heavy Weight Dropping H. |
|---|---|---|---|---|
| L Traffic | 2 ton | 0.84 ton | 2.84 ton | 4.90 cm |
| A Traffic | 3 ton | 1.26 ton | 4.26 ton | 7.30 cm |
| B Traffic | 5 ton | 2.10 ton | 7.10 ton | 12.20 cm |
| C Traffic | 8 ton | 3.36 ton | 11.36 ton | 19.50 cm |
| D Traffic | 12 ton | 5.04 ton | 17.04 ton | 29.30 cm |

As shown above, any loads required can be set and generated by varying the dropping height of the heavy weight or the weight of the heavy weight. The dynamic added loads generated corresponding to the designed wheel loads on a road surface having a standard flatness are obtained as described above. Thus, the induced ground vibration level is measured at the road side by giving a specified dynamic added load to the paved road surface. The load giving position is generally at the outer wheel traveling portion of the outer lane and each measuring position of the vibration level is located at 2 m, 5 m, 10 m, 15 m and 20 m from the central point of the load giving place (vibration origin) in the direction of a right angle from the vibration origin and a curved line connecting each maximum value of the vibration level wave at each measuring point. The vibration level at the above each distance from the vibration origin is compared with a standard value of the vibration level measured separately and the vibration properties of paved road construction or the pavement damping function of the pavement can be calculated therefrom for evaluation.

On the other hand, in the case that the ground is a cushion course of architectural construction base, the load corresponding to the seismic intensity is to be given to the ground and the vibration generated is measured as the origin of the vibration in terms of vibration level at each distance as described above. The measured vibration level is compared with a standard vibration level measured separately and the vibration properties of the cushion course of the architectural construction base can be calculated therefrom.

As described above, in the case that the ground is a paved road construction, a heavy weight is fallen on the paved road surface from a specified height vertically, and any designed wheel loads corresponding to the L to D Traffics listed in Table 1 may be acted on by varying the falling height and the mass of the heavy weight according to the present invention. The dynamic added load generated corresponding to the designed wheel load while vehicles are traveling on a road surface having the standard flatness can be acted on the road surface. In this case, when one vehicle is traveling, the heavy weight is acted on only once. When a plurality of vehicles are traveling, the heavy weight is acted on once per unit time continuously, for instance, once per about a second repeatedly. Then, the vibration generated is measured as a vibration level at each distance from the vibration origin and the vibration properties of pavement can be calculated from the measured values.

In the case that the ground is a cushion course of architectural construction base, the load corresponding to a seismic intensity of earthquake can be acted on a ground by dropping a heavy weight vertically by means of the vibration generating equipment and by changing the dropping height or the mass of the the heavy weight. Then, the vibration properties of the ground can be calculated from the measured values obtained by measuring the vibration generated as a vibration level at each distance from the vibration origin.

We claim:

1. A ground vibration properties detection equipment comprising a vibration generating unit and a vibration level measuring unit, the vibration generating unit comprising a driving motor, a driving sprocket wheel mounted on output shaft of the driving motor, a driven sprocket wheel provided in a spaced relationship with the driving sprocket wheel, a first roller chain provided between the driving sprocket wheel and the driven sprocket wheel, a heavy weight lifting driving sprocket wheel to which a rotation force of the driven sprocket wheel is transferred, a heavy weight lifting driven sprocket wheel provided above the heavy weight lifting driving sprocket wheel, a second roller chain provided between the heavy weight lifting driving sprocket wheel and the heavy weight lifting driven sprocket wheel, an electromagnetic clutch mounted between the driven sprocket wheel and the heavy weight lifting driving sprocket wheel and to shut or transfer the rotation force by means of a signal from a limit switch preset at an upper position and lower position, a wire rope fastening fitting mounted on the second roller chain and moveable in an area only between a lower area close to the heavy weight lifting driving sprocket wheel and an upper area close to the heavy weight lifting driven sprocket wheel, a lifting wire rope an end of which is connected with the wire rope fastening fitting and is hung by means of a wire rope guide roller and a heavy weight hung on the other end of the lifting wire rope, and the vibration level measuring unit comprising a sensor to sense vibration levels at distances from the place where the heavy weight of the vibration generating unit is dropped, a vibration level meter connected with the sensor to measure the vibration level and a vibration level recorder connected with the vibration level meter to record the vibration level measured.

2. The ground vibration properties detection equipment according to claim 1 wherein a load cell is mounted on the lower portion of the heavy weight.

3. The ground vibration properties detection equipment according to claim 1 wherein a heavy weight guide unit having a receptive portion is provided along the heavy weight dropping direction and the heavy weight is formed with a spline on each side thereof to be received in the receptive portion.

4. The ground vibration properties detection equipment according to claim 1 wherein a cylindrical frame having a larger diameter than that of the heavy weight and both open ends is placed so as to have the center line of the frame substantially coincide with the center of the heavy weight and a plasticized material is filled in the frame to absorb an undulation of the ground surface for correction and a sound absorbent is placed thereon.

* * * * *